(12) United States Patent
Huang et al.

(10) Patent No.: US 8,735,118 B2
(45) Date of Patent: May 27, 2014

(54) XYLANASE COMPOSITION WITH INCREASED STABILITY

(75) Inventors: Yahui Huang, Hsinchu (TW); Chunhui Hsieh, Ershui Township, Changhua County (TW); Hsuanyu Lai, New Taipei (TW)

(73) Assignee: YFY Biopulp Technology Limited, Tortola (VG)

( * ) Notice: Subject to any disclaimer, the term of this patent is extended or adjusted under 35 U.S.C. 154(b) by 0 days.

(21) Appl. No.: 13/505,310

(22) PCT Filed: Nov. 24, 2009

(86) PCT No.: PCT/CN2009/075103
§ 371 (c)(1),
(2), (4) Date: May 1, 2012

(87) PCT Pub. No.: WO2011/063558
PCT Pub. Date: Jun. 3, 2011

(65) Prior Publication Data
US 2012/0214220 A1 Aug. 23, 2012

(30) Foreign Application Priority Data
Nov. 24, 2009 (WO) ................ PCT/CN2009/075103

(51) Int. Cl.
*C12N 9/96* (2006.01)

(52) U.S. Cl.
USPC .......................................... 435/188; 435/200

(58) Field of Classification Search
USPC ................................................ 435/188, 200
See application file for complete search history.

(56) References Cited

U.S. PATENT DOCUMENTS

| | | | | |
|---|---|---|---|---|
| 7,060,482 | B1 * | 6/2006 | Sung et al. | 435/200 |
| 7,157,416 | B2 | 1/2007 | Becker et al. | |
| 2004/0053238 | A1 * | 3/2004 | Hseu et al. | 435/6 |
| 2012/0288915 | A1 * | 11/2012 | Huang et al. | 435/200 |

FOREIGN PATENT DOCUMENTS

| | | | |
|---|---|---|---|
| TW | 200720435 | 1/2006 | ............... C12N 9/00 |
| WO | 0029587 A1 | 5/2000 | |

OTHER PUBLICATIONS

Fisk R. et al. Development of a Method for the Stabilization and Formulation of Xylanase from Trichoderma Using Experimental Design. Studies in Organic Chemistry 47:323-328, 1992.*
Breccia J. et al. Thermal Stabilization by Polyols of Beta Xylanase from Bacillus amyloliquefaciens. J Chemical Technology & Biotechnology 71(3)241-245, 1998.*
George S. et al. A Novel Thermostable Xyalanse from Thermomonospora sp. Bioresource Technology 78(3)221-4, Jul. 2001.*
Fisk et al. 1992. Development of a Method for the Stabilization and Formulation of Xylanase from Trichoderma Using Experimental Design. Studies in Organic Chemistry, 47: 323-328; Asther et al. 1990. Increased thermal stability of *B. licheniformis alpha-amylase* in the presence of various additives. Enzyme and Microbial Technology. 12: 902.905; Trinci et al. 1994. Anaerobic fungi in herbivorous animals. Mycol. Res. 98: 129-152.
Viswanathan et al. 1995. Effect of polyols on heat inactivation of *Aspergillus niger van Teighem inulinase*. Letters in Applied Microbiology, 21: 282-284; and Georis et al. 1999. Sequence, overproduction and purification of the family 11 endo-beta-1,4-xylanase encoded by the xyl1 gene of *Streptomyces sp.* S38. Gene 237:123-33.
Supplementary European Search Report and Opinion, Apr. 2, 2013.
Mountfort, et al., Production of xylanase by the ruminal anaerobic fungus *Neocallimastix frontalis*, Applied and Environmental Microbiology, vol. 55, No. 4, pp. 1016-1022 (1989).
Mesta, L. et al., Construction of a chimeric xylanase using multidomain enzymes from *Neocallimastix frontalis*, Enzyme and Microbial Technology, vol. 29, No. 6-7, pp. 456-463 (2001).
Duarte, Marta Cristina Teixeira, et al., Characterization of Alkaline Xylanases From *Bacillus Pumilus*, Brazilian Journal of Microbiology, vol. 31, pp. 90-94 (2000).
Fisk, R. S., et al., Development of a Method for the Stabilization and Formulation of Xylanase from *Trichoderma* Using Experimental Design, Stability and Stabilization of Enzymes, pp. 323-328 (1992), Elsevier Science Publishers B.V.

* cited by examiner

*Primary Examiner* — Ralph Gitomer
(74) *Attorney, Agent, or Firm* — Michael W. Ferrell; Ferrells, PLLC; Anna L. Kinney

(57) ABSTRACT

A xylanase composition and a method for manufacturing the xylanase composition are provided, wherein the xylanase composition comprises a xylanase and a stabilizer, and the xylanase is from an anaerobic fungus, the stabilizer comprises a polyol, and the content of the polyol is at least 40 wt %, based on the total weight of the xylanase composition.

4 Claims, 2 Drawing Sheets

XYLANASE COMPOSITION WITH INCREASED STABILITY

This application claims priority to PCT Patent Application No. PCT/CN2009/075103 filed on Nov. 24, 2009, the disclosure of which is incorporated herein by reference in its entirety.

CROSS-REFERENCES TO RELATED APPLICATIONS

Not applicable.

BACKGROUND OF THE INVENTION

1. Field of the Invention

The present invention relates to a xylanase composition with increased stability, and the method for manufacturing the same.

2. Descriptions of the Related Art

Enzymes are proteins which can function as bio-catalysts and can be widely applied in various chemical reactions to increase the rate of reaction.

Inactive enzymes are costly for researchers and factory owners because once an enzyme is inactivated and loses its function, it cannot exert its intrinsic catalytic action. As a result, researchers or factory owners have to pay additional costs to increase the amount of the enzyme used or purchase new enzymes for replacement to achieve the desired efficiency.

Therefore, a method or a formulation that prevents enzymes from being inactivated due to environment factors, such as high temperature, or increases the stability of enzymes during storage or transport is urgently desired in the industry.

Xylanase is the main enzyme that degrades hemicellulose among sugar hydrolysis enzymes, and is widely applied in various fields such as foods, animal feeds, textiles or papermaking. For example, xylanase may be used to treat chicken feed to degrade anti-nutrient factors in the feed, thereby, promoting the uptake of nutrient and the growth of chickens. In addition, if xylanase is added in the dough, the mechanical strength of the dough may be improved, and its appearance and storability can also be improved accordingly.

A method for increasing the stability of xylanase from aerobic fungi has been disclosed in the literature, which improves the storability of xylanase by using a formulation comprising a polyol, salts and antibiotics (Fisk et al. 1992. Development of A Method for the Stabilization and Formulation of Xylanase from *Trichoderma* Using Experimental Design. *Studies in Organic Chemistry*, 47: 323-328, which is incorporated hereinto by reference). However, according to the literature, the stabilizing effect (e.g., the stabilizing duration and temperature) provided by the formulation is quite limited. The activity of xylanase from an aerobic fungus, *Trichoderma*, was at about 80% after 42 hours under 48° C.

As known by persons with ordinary knowledge in the art of enzymes, different enzymes have different characteristics, such as the structure, heat resistance, or optimum storage condition, etc. The interaction between different enzymes and the same compound or formulation is also different. Therefore, it has been indicated in literatures that for different enzymes, the same component or formulation cannot provide the same stabilizing effect, and polyols do not necessarily provide a stabilizing effect (Asther et al. 1990. Increased thermal stability of *B. licheniformis* alpha-amylase in the presence of various additives. *Enzyme and Microbial Technology.* 12: 902-905, which is incorporated hereinto by reference).

Among the known xylanses from different sources, xylanases from anaerobic fungi (also called rumen fungi) are the most interesting because anaerobic fungi generally grow in the rumen (such as the digestive tract of ruminants or herbivores with a single stomach) in which competition stress for survival is high. Thus, these fungi have evolved to produce xylanases with high activity (Anthony et al. 1994. Anaerobic fungi in herbivorous animals. *Mycol. Res.* 98: 129-152, which is incorporated hereinto by reference). Compared to general xylanases, xylanases from anaerobic fungi are more widely applicable due to their advantages, such as high enzyme activity, high specificity, heat resistance, etc. Hence, a method for preserving xylanases from anaerobic fungi effectively is required for persons in this field to prevent the enzyme activity from decreasing during the storage.

The present invention provides a composition for increasing the stability of xylanase from anaerobic fungi. The inventors of the present application found that a composition comprising polyols with specific components and ratio can achieve the effect of significantly increasing enzyme storability.

SUMMARY OF THE INVENTION

The primary objective of the present invention is to provide a xylanase composition with increased stability, comprising a xylanase and a stabilizer comprising a polyol.

Another objective of the present invention is to provide a method for manufacturing a xylanase composition with increased stability, comprising providing a xylanase and a stabilizer comprising a polyol, and mixing the xylanase and the stabilizer to form a xylanase composition.

The first objective of the present invention is to provide a method for manufacturing a xylanase composition with increased stability, comprising the following:
providing a xylanase;
providing a stabilizer, comprising a polyol; and
mixing the xylanase and the stabilizer to form a xylanase composition;
wherein the xylanase is from an anaerobic fungus, and the content of the polyol is at least 40 wt %, based on the total weight of the xylanase composition.

The second objective of the present invention is to provide a xylanase composition, comprising a xylanase and a stabilizer, wherein the xylanase is from an anaerobic fungus, the stabilizer comprises a polyol, and, based on the total weight of the xylanase composition, the content of the polyol is at least 40 wt %.

The detailed technology and preferred embodiments implemented for the subject invention are described in the following paragraphs accompanying the appended drawings for people skilled in this field to well appreciate the features of the claimed invention.

DETAILED DESCRIPTION OF THE INVENTION

Figure 1:
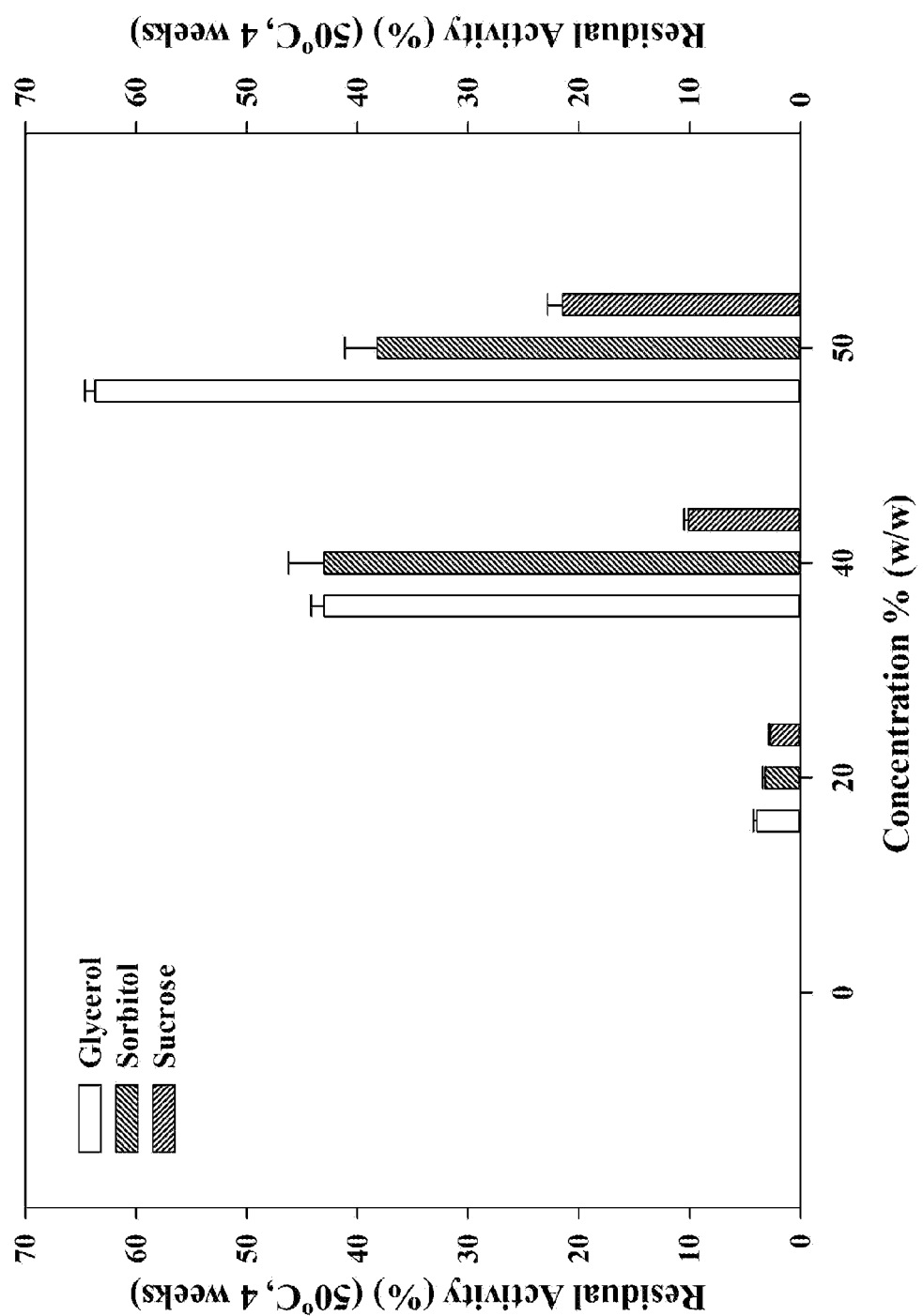
FIG. 1 is a bar chart showing the enzyme stabilizing effect of xylanase compositions comprising different polyols at different concentrations.

Unless otherwise stated herein, the terms "a (an)", "the" or the like used in this specification (especially in the Claims hereinafter) shall be understood to encompass both the singular and plural form.

In the context, the term "stability of an enzyme" is defined as the resistance or tolerance of the enzyme to environmental factors, especially temperature. Generally, the stability of an enzyme can be determined by the decay rate of enzyme activity under a specific environment. The slower the decay rate, the higher the enzyme stability.

As described above, xylanase is widely applied in fields such as food, animal feed, textile, papermaking, etc. For papermaking application, it is known that when xylanase is added into the pulp during the process of pulp making, the power required for pulping can be significantly reduced, and the energy consumption can be also reduced accordingly. Furthermore, a large amount of chlorine-containing bleach is usually required in the process of pulp bleaching; however, chlorine leads to the generation of highly toxic organic chloride compounds, resulting in waste disposition problems. If the pretreatment by xylanase is performed before the bleaching process, the amount of chlorine-containing substances used can be significantly reduced, and the waste disposition problems can be effectively resolved. Therefore, if xylanase can perform its function under high temperature and does not degrade cellulose, the reaction rate of pulp treatment can be improved without damaging cellulosic fibers. In addition, if xylanase can specifically hydrolyze hemicellulose (i.e., without hydrolyzing cellulose) and is heat-resistant, the paper making process can be improved more effectively thereby.

Because xylanases from anaerobic fungi has the desired high specificity and heat-resistance properties, it is important to also elevate the stability of these enzymes. Thus, the present invention provides a xylanase composition, comprising a xylanase and a stabilizer, wherein the xylanase is from, for example, *Neocallimastix* genus, *Caecomyces* genus, or *Piromyces* genus, *Orpinomyces* genus, *Cyllamyces* genus, *Anaeromyces* genus, etc., and is preferably from *Neocallimastix* genus. In the preferred embodiment of the present invention, a xylanase from *Neocallimastix frontalis* is used to prepare the xylanase composition.

In addition, the xylanase in the present invention may be obtained by isolating natural xylanase or by an artificial synthesizing method (such as using genetic engineering or a peptide synthesizer). Furthermore, for an isolated or synthesized xylanase, molecular biology technique may be applied to further modify its gene to increase its activity, specificity and/or stability. For example, when xylanase from the anaerobic fungus *Neocallimastix frontalis* is used to prepare the composition of the present invention, the removal of the dockerin domain in the xylanase gene may be performed before expression of the xylanase gene to further increase the stability and activity of xylanase. Specifically, the removal of the dockerin domain in the xylanase gene may be performed using the following method. First, a polymerase chain reaction (PCR) is used to amplify the xylanase gene of *Neocallimastix frontalis* (about 1,011 bp), and then restriction enzymes are used to remove the dockerin domain in the xylanase gene. The generated gap is eliminated with a ligase. After that, another polymerase chain reaction is conducted to amplify the xylanase gene that does not contain a dockerin domain (about 729 bp), thereby, obtaining the gene of xylanase that has high activity and stability. The above method can be seen in Taiwan Patent Application Publication No. 200720435, which is incorporated hereinto by reference.

The stabilizer in the composition of the present invention comprises a polyol. The term "polyol" indicates any compound with two or more hydroxyl groups. For example, but not limited thereto, the polyol in the composition of the present invention may consist of one or more $C_3$-$C_{12}$ polyols, such as propylene glycol, glycerol, erythrose, sorbitol, glucose, mannose, fructose, galactose, sucrose, maltose, lactose, and the like. Preferably, the polyol in the composition of the present invention is selected from the group consisting of glycerol, sorbitol, sucrose, and combinations thereof.

In the xylanase composition of the present invention, based on the total weight of the xylanase composition, the content of the polyol is at least 40 wt %, preferably at least 50 wt %, more preferably at least 60 wt %, and most preferably at least 80 wt %.

In an example of the present invention, when the xylanase compositions comprising a polyol at different contents were used to stabilize xylanase, it was found that the stabilizing effect of the polyol on xylanase from the anaerobic fungus is approximately proportional to the content of the polyol in the composition. In other words, the higher the content of the polyol in the composition, the better the stabilizing effect of the composition on xylanase.

The discovery above is quite different from the findings in the existing literatures. For example, Fisk et al. uses a polyol to stabilize xylanase from an aerobic *Trichoderma* fungus, and discloses that a composition comprising glycerol at a content of 40% has the best stabilizing effect, but when the content of glycerol is higher above 40%, the stabilizing effect provided is not increased but rather decreased with the increase of the content of glycerol (Fisk et al. 1992. Development of A Method for the Stabilization and Formulation of Xylanase from *Trichoderma* Using Experimental Design. *Studies in Organic Chemistry*, 47: 323-328, which is incorporated hereinto by reference). In other words, according to the literature, the stabilizing effect of a polyol is not proportional to its content, and the content of the polyol is preferably not more than 40%.

In addition, the other literature also indicates that the enzyme stabilizing effect of a polyol depends on the number of hydroxyl groups on the polyol, and the stabilizing effect is better with the increase of the number of hydroxyl groups (Viswanathan et al. 1995. Effect of polyols on heat inactivation of *Aspergillus niger* van Teighem inulinase. *Letters in Applied Microbiology*, 21: 282-284, which is incorporated hereinto by reference). However, as shown in the following examples, compared to sorbitol (with six hydroxyl groups) and sucrose (with eight hydroxyl groups), glycerol (with three hydroxyl groups) can provide a better stabilizing effect on xylanase from *Neocallimastix frontalis*.

The xylanase composition of the present invention may further comprise other additives as long as the additives do not deteriorate the activity of xylanase and have no substantially adverse influence on the stabilizing effect of the composition. In an embodiment of the present invention, in addition to a xylanase and a polyol, the xylanase composition further comprises water, so that the composition is in the form of an enzyme solution (i.e., xylanase dissolved in water).

The xylanase composition of the present invention can be applied to a variety of fields, such as food, animal feed, textile, papermaking, etc.

The present invention also provides a method for manufacturing a xylanase composition with increased stability, comprising providing a xylanase; providing a stabilizer comprising a polyol; and mixing the xylanase and the stabilizer to form a xylanase composition. The xylanase, stabilizer, polyol and xylanase composition involved in the method of the present invention are those as described above.

The method of the present invention may further comprise adding water into at least one of the following substances: xylanase, the stabilizer, and the xylanase composition.

Specifically, water may be used to adjust the properties of components in the composition of the present invention to achieve the following purposes: 1) by mixing xylanase and water, xylanase may be in the form of an enzyme solution, and the activity unit of xylanase can be controlled; 2) the concentration of a polyol in the stabilizer may be adjusted by mixing the stabilizer and water; and 3) the final adjustment may be performed by adding water into the xylanase composition. In an embodiment of the present invention, xylanase from an anaerobic fungus *Neocallimastix frontalis* was mixed with glycerol to prepare a xylanase composition, and water was then used to adjust the activity unit of xylanase and make the final content of glycerol in the composition be 90 wt %. The composition was stored for two weeks and eight weeks respectively under 50° C., and xylanase contained therein still had the residual activity of 97±4.8% and 59.6±4.7%, respectively.

Therefore, compared to the conventional art, the xylanase composition of the present invention may provide xylanase with a better stabilizing effect under common storage conditions (e.g., room temperature) or even more stringent conditions (e.g., high temperature), thereby extending the storage period of xylanase.

The detailed technology and preferred embodiments implemented for the present invention are described in the following paragraphs; however, the scope of the present invention is not limited thereby.

Example 1

Preparation of the Xylanase Compositions

First, xylanase compositions comprising glycerol with different contents were prepared by adding glycerol into an enzyme solution containing xylanase from an anaerobic fungus *Neocallimastix frontalis* (i.e., an solution in which xylanase was dissolved in water, and the activity of xylanase was about 100,000 unit (U)/ml), and followed by stirring the mixture, so that the final content of glycerol, based on the total weight of the xylanase composition, was about 20 wt %, 40 wt % or 50 wt %, respectively.

Second, xylanase compositions comprising 20 wt %, 40 wt % or 50 wt % of sorbitol or sucrose were prepared with the same method and ratio. The control group (i.e., a xylanase composition comprising 0 wt % of a polyol) was prepared by substituting glycerol, sorbitol or sucrose with water.

Measurement of the Activity of Xylanase in the Compositions

The measurement of the activity of xylanase in the compositions was conducted based on the following mechanism. After a dinitrosalicyclic acid (DNS) solution and the reducing sugars generated from hydrolysis by xylanase are heated together, a brown red amino compound is formed, and a colorimetric method is used to measure the content of the reducing sugars in the sample to determine the activity of xylanase.

The detailed method for measuring activity was based on Georis' method (Georis et al. 1999. Sequence, overproduction and purification of the family 11 endo-beta-1,4-xylanase encoded by the xyl1 gene of *Streptomyces* sp. S38. Gene 2437:123-33, which is incorporated hereinto by reference). In this method, 90 µl of 3 wt % of xylan (oat spelts xylan dissolved into a tris(hydroxymethyl) aminomethane or (Tris) buffer solution of 25 mM, pH 8.0) was used as a substrate for the enzyme reaction, and was uniformly mixed with 10 µl of the above xylanase compositions, of which the content was properly adjusted. After the mixture was reacted at 60 ° C. for 5 minutes, 125 µl of a dinitrosalicyclic acid reagent was added to terminate the reaction, and the resulting mixture was then reacted at 98° C. for 5 minutes to undergo the color reaction. Finally, the absorbance was measured at wavelength of 540 nm to calculate the content of the reducing sugars, and the activity of xylanase in the compositions was thus determined, wherein one (1) activity unit (U) is defined as the amount of the enzyme required for releasing/hydrolyzing 1 µmole of reducing sugars per minute per ml.

Determination of the Stability of Xylanase

First, before this test was conducted, the original activity of xylanase in the xylanase compositions prepared above was determined, and the measured original activity was defined as residual activity of 100%. The xylanase compositions were then set in the environment at 50° C. for four weeks (i.e., continuously stored for four weeks).

After four weeks, the activity of xylanase in the xylanase compositions was determined respectively, and the residual activity of xylanase was calculated using the following formula:

Residual Activity (%)=(the activity of xylanase after storage/the original activity of xylanase)×100%.

The higher the residual activity of xylanase measured, the better the enzyme stabilizing effect of a xylanase composition. The measurement results of the enzyme stability are shown in Table 1 and FIG. 1 below.

TABLE 1

| | Polyol | | |
|---|---|---|---|
| | Glycerol | Sorbitol | Sucrose |
| Content (wt %) | Residual activity of xylanase (%) | | |
| 0 | 0 | 0 | 0 |
| 20 | 3.9 ± 0.3 | 3.2 ± 0.3 | 2.8 ± 0.1 |
| 40 | 43 ± 1.2 | 43 ± 3.2 | 10.1 ± 0.3 |
| 50 | 63.7 ± 0.9 | 38.2 ± 3 | 21.5 ± 1.4 |

It can be seen from FIG. 1 and Table 1 that for the composition without a stabilizer, after being stored at 50° C. for four weeks, the residual activity of xylanase was 0%, indicating that the xylanase had completely lost its activity. However, if a stabilizer, such as a polyol like glycerol, sorbitol, sucrose, etc., was added into the composition, the residual activity of xylanase was significantly increased, and the increase effect was approximately proportional to the content of the polyol.

In addition, for the polyols, glycerol showed the best improvement for the stability of the enzyme, and after continuously being stored at 50° C. for four weeks, the composition containing 50 wt % glycerol retained a residual activity of 63.7±0.9%.

Example 2

First, xylanase compositions comprising glycerol at different contents were prepared by adding glycerol into a solution containing xylanase from an anaerobic fungus *Neocallimastix frontalis* (i.e., a solution in which xylanase, with an activity of 100,000 unit (U)/ml, was dissolved in water), and then followed by stirring the mixture, so that the final content of glycerol, based on the total weight of the xylanase composition, was 20 wt %, 40 wt %, 50 wt %, 70 wt %, or 90 wt %, respectively. The control group (i.e., a xylanase composition comprising 0 wt % of a polyol) was prepared by substituting glycerol with water.

Second, the activity and stability of xylanase in the compositions prepared above were measured by the same methods as described in Example 1. The xylanase compositions were stored in the environment at 50° C. for eight weeks (i.e., continuously stored for eight weeks), and the samples were collected every two weeks to measure the activity of xylanase in the compositions. The residual activity was thus calculated.

The measurement results of the enzyme stability are shown in Table 2 and FIG. 2 below.

TABLE 2

| Content (wt %) | Polyol Glycerol Residual activity of xylanase (%) | | | | |
| --- | --- | --- | --- | --- | --- |
| | 1 week | 2 weeks | 4 weeks | 6 weeks | 8 weeks |
| 0 | 1 | 0 | 0 | 0 | 0 |
| 20 | | 21.9 ± 1.6 | 3.9 ± 0.3 | 0.7 ± 0 | 0.2 ± 0 |
| 40 | | 72.8 ± 4.2 | 43 ± 1.2 | 27.3 ± 0.2 | 20.7 ± 0.6 |
| 50 | | 84.2 ± 3 | 63.7 ± 0.9 | 46.7 ± 2 | 34.3 ± 1.0 |
| 70 | | 101 ± 5.4 | 81.1 ± 6.3 | 73.7 ± 5.2 | 58.4 ± 2.6 |
| 90 | | 97 ± 4.8 | 76.8 ± 3 | 73.8 ± 5.3 | 59.6 ± 4.7 |

Figure 2:
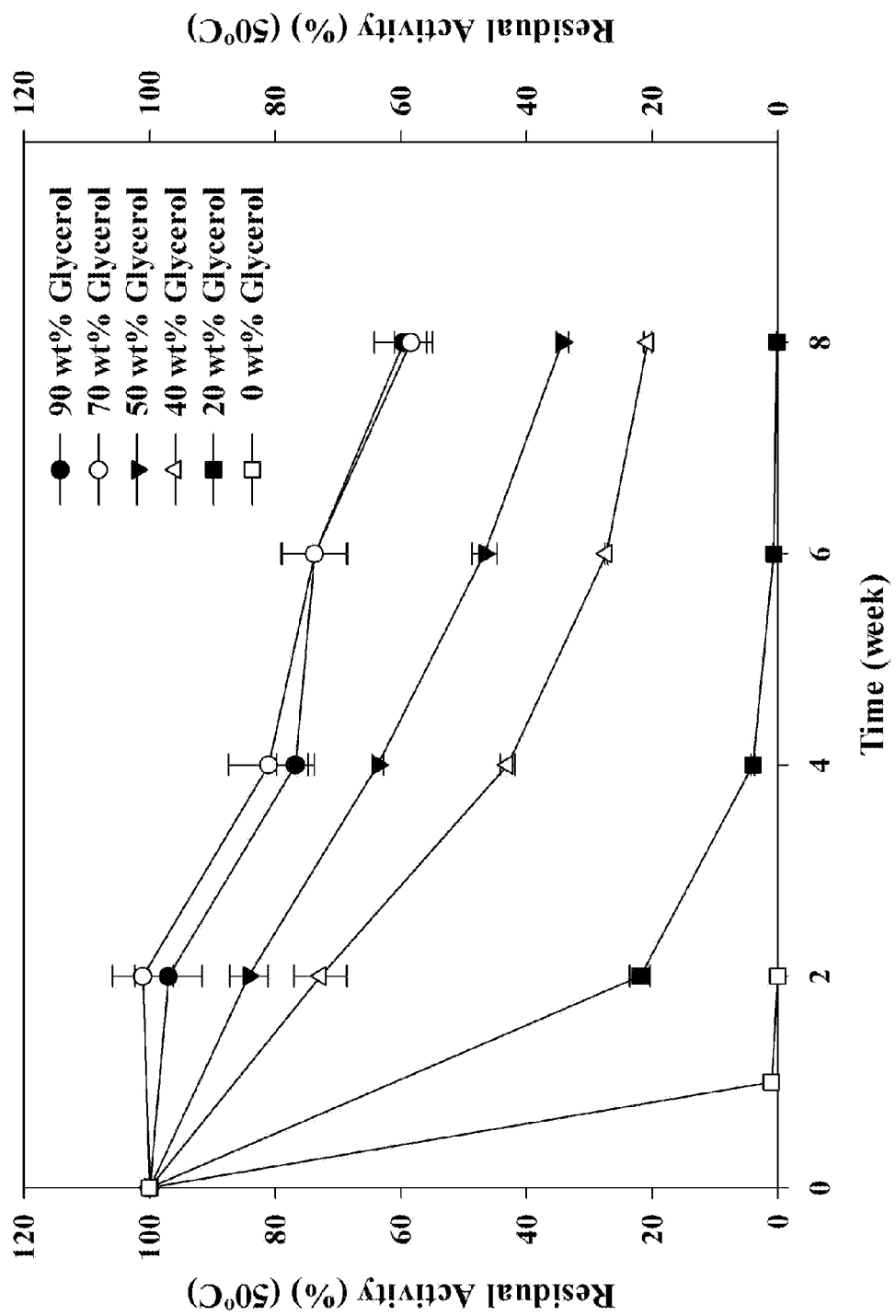
FIG. 2 is a curve chart showing enzyme stabilizing effect of xylanase compositions comprising glycerol at different concentrations under 50° C.

It can be seen from FIG. 2 and Table 2 that if no glycerol was added into the xylanase composition, the residual activity of xylanase, after being continuously stored at 50° C. for one week, remained about 1%. However, if glycerol was added into the xylanase composition, the activity of xylanase can be maintained longer. After continuously being stored at 50° C. for eight weeks, in the xylanase compositions comprising different glycerol contents, the residual activity of the enzyme, from the lowest to the highest, was 20 wt %: 0.2±0%; 40 wt %: 20.7±0.6%; 50 wt %: 34.3±1.0%; 70 wt %: 58.4±2.6%; and 90 wt %: 59.6±4.7%, respectively.

In addition, it can be seen from FIGS. 1 and 2 and Tables 1 and 2 that as the polyol content increased, the residual activity of xylanase also increased, which illustrates that the stabilizing effect of the xylanase composition on xylanase was approximately proportional to the content of a polyol. When the content of glycerol was higher than 70 wt %, this proportional relation became less obvious.

Examples 1 and 2 proved that the composition of the present invention can provide an excellent stabilizing effect on xylanase from the anaerobic fungus, and thus, may extend the storage period of xylanase.

The above disclosure is related to the detailed technical contents and inventive features thereof People skilled in this field may proceed with a variety of modifications and replacements based on the disclosures and suggestions of the invention as described without departing from the characteristics thereof Nevertheless, although such modifications and replacements are not fully disclosed in the above descriptions, they have substantially been covered in the following claims as appended.

What is claimed is:

1. A xylanase composition comprising a xylanase and a stabilizer, wherein the xylanase is from *Neocallimastix* genus, the stabilizer comprises a polyol, and the content of the polyol is at least 60 wt % based on the total weight of the xylanase composition, wherein the polyol is selected from the group consisting of glycerol, sorbitol, sucrose, and combinations thereof.

2. The composition according to claim 1, wherein the xylanase is from *Neocallimastix frontalis*.

3. The composition according to claim 1, wherein the polyol is glycerol.

4. The composition according to claim 1, wherein the content of the polyol is at least 80 wt % based on the total weight of the xylanase composition.

* * * * *